United States Patent
Schuman

(10) Patent No.: US 12,208,281 B2
(45) Date of Patent: Jan. 28, 2025

(54) RADIATION ONCOLOGY HEAD POSITIONING EQUIPMENT AND RADIO-ONCOLOGY PATIENT POSITIONING DEVICE

(71) Applicant: LANDRATSAMT ORTENAUKREIS KORPERSCHAFT DES OFFENTLICHEN RECHTS, Offenburg (DE)

(72) Inventor: Dirk Schuman, Offenburg (DE)

(73) Assignee: LANDRATSAMT ORTENAUKREIS KORPERSCHAFT DES OFFENTLICHEN, Offenburg (DE)

( * ) Notice: Subject to any disclaimer, the term of this patent is extended or adjusted under 35 U.S.C. 154(b) by 737 days.

(21) Appl. No.: 17/632,184

(22) PCT Filed: Nov. 7, 2018

(86) PCT No.: PCT/EP2018/080505
§ 371 (c)(1),
(2) Date: Jul. 26, 2022

(87) PCT Pub. No.: WO2019/092039
PCT Pub. Date: May 16, 2019

(65) Prior Publication Data
US 2022/0370826 A1    Nov. 24, 2022

(30) Foreign Application Priority Data

Nov. 7, 2017    (DE) .................... 10 2017 126 025.0

(51) Int. Cl.
*A61N 5/10*     (2006.01)
*A61B 6/04*     (2006.01)
*A61B 90/10*    (2016.01)

(52) U.S. Cl.
CPC .............. *A61N 5/10* (2013.01); *A61B 6/04* (2013.01); *A61B 6/0407* (2013.01);
(Continued)

(58) Field of Classification Search
CPC .............. A61N 5/10; A61N 2005/1097; A61N 5/1049; A61N 5/1064; A61B 6/0492;
(Continued)

(56) References Cited

U.S. PATENT DOCUMENTS 5,775,337 A     7/1998  Hauger et al.
10,470,957 B1 * 11/2019  Denis ...................... A61G 7/07
(Continued)

FOREIGN PATENT DOCUMENTS

DE  69821368 T2      6/2004
EP   2583634 A1 *   4/2013  ............. A61B 90/14
WO  WO-0027331 A2 * 5/2000  ........... A61B 6/0421

OTHER PUBLICATIONS

German Patent Office: "Prüfungsbescheid Exam Notice"; May 15, 2018.

*Primary Examiner* — Adam C Ortiz
*Assistant Examiner* — Madison Emanski
(74) *Attorney, Agent, or Firm* — Bryan W. Bockhop; Bockhop Intellectual Property Law, LLC

(57) ABSTRACT

A radio-oncology patient positioning device comprising a torso support portion adapted to support the torso of a patient, having
  first positioning members configured to releasably arrange
  a knee positioning means; and/or
  a pelvic positioning device; and
  a shoulder support region comprising second positioning members adapted to releasably arrange
  a neck positioning means; and/or (Continued)

a shoulder positioning device;
characterized by:
   a head support portion;
    wherein the head support portion is pivotally mounted, by means of at least one hinge to the torso support portion or a base plate on which the torso support portion is mounted; and
      wherein the head support portion is adapted such that a radio-oncological head positioning device is detachably attachable to the head support portion, wherein a occipital mask and/or a face mask is arrangeable to the head positioning device.

18 Claims, 7 Drawing Sheets

(52) U.S. Cl.
CPC ....... *A61B 6/0428* (2013.01); *A61B 2090/101* (2016.02); *A61N 2005/1097* (2013.01)

(58) Field of Classification Search
CPC . A61B 90/14; A61B 6/0421; A61B 2090/101; A61B 2090/571; A61B 6/0407; A61B 6/0487; A61B 90/18; A61B 90/50; A61B 90/57; A61G 13/12; A61G 13/121; A61G 13/122; A61G 13/1245; A61F 5/3769; A61F 5/3707
USPC ...................... 128/845, 869; 5/622, 637, 601
See application file for complete search history.

(56) References Cited

U.S. PATENT DOCUMENTS

| | | | |
|---|---|---|---|
| 2009/0308400 A1* | 12/2009 | Wilson | A61B 90/57 |
| | | | 128/845 |
| 2011/0107515 A1 | 5/2011 | Brunker et al. | |
| 2015/0053213 A1 | 2/2015 | Neiberding | |

* cited by examiner

RADIATION ONCOLOGY HEAD POSITIONING EQUIPMENT AND RADIO-ONCOLOGY PATIENT POSITIONING DEVICE

The present invention relates to an improved radio-oncological head positioning device and an improved radio-oncological patient positioning device that positions the patient in a radio-oncological device more reproducibly and with less backlash.

PRIOR ART

In order to irradiate predetermined tissue of a patient during a radio-oncological treatment, patient positioning devices are used to position the patient and in particular the tissue to be irradiated reproducibly with respect to the radiation source. This ensures that, on the one hand, the tissue affected by a tumor, for example, is irradiated, but that no healthy tissue is damaged.

So-called occipital masks, facial masks and whole-skull masks are used in particular to treat affected tissue in the head. Furthermore, neck masks and shoulder masks are known.

With prior art positioning aids, various body parts can be positioned in radio-oncology by means of suitable devices or by means of devices to be attached directly on the radiation table. Any attachment of devices can cause deviations in the area of the irradiation field and beyond, which can lead to undesirable inaccuracies. This also has a higher time scope as well as more physical stress for the personnel.

Radio-oncology patient positioning devices of the prior art can be modularly assembled from a plurality of components.

SUMMARY OF THE INVENTION

Therefore, the object of the invention is to provide a radio-oncological head positioning device and a radio-oncological patient positioning device with improved reproducibility of patient positioning.

The object of the invention is solved by a radio-oncological patient positioning device according to claim 1. The dependent claims claim preferred embodiments.

A radio-oncology patient positioning device according to the present invention comprises a torso support region configured to support the torso of a patient. The torso support region comprises first positioning members adapted to releasably arrange a knee positioning device and/or a pelvis positioning device. The torso support region comprises a shoulder support region comprising second positioning members adapted to releasably arrange a neck positioning means and/or a shoulder positioning means. The patient positioning device further comprises a head support portion, wherein the head support portion is pivotally arranged on the shoulder support portion or on a base plate by means of at least one joint, on which the torso support portion is arranged, and wherein the head support portion is configured such that a radio-oncological head positioning device is detachably attachable to the head support portion, wherein a occipital mask and/or a face mask is arrangeable on the head positioning device. The head support area can be fixedly, i.e., not detachably, arranged on the torso support area in use.

In this way, the patient is positioned precisely and reproducibly during the entire irradiation period. The individual additional components can be adapted exactly to the patient by the positioning elements in each case at the beginning of the treatment period and their position on the patient positioning device is maintained until the end of the treatment period. In addition, the time required for the individual irradiations is reduced, since the various irradiation devices are positioned directly and without modification, as well as the physical effort required of the staff due to the lightweight carbon patient positioning device.

The torso support area is designed to support the torso of a patient. The head support area is designed to support a patient's head. The head support portion is fixedly disposed on the torso support portion or the base plate, and is pivotally disposed on the torso support portion by means of at least one joint (hinge). The radio-oncological head positioning device is detachably arranged on the head support area.

As a result of the head support area being arranged fixedly by means of at least one hinge so as to be pivotable on the torso support area or on the base plate, tolerances and the backlash are reduced, thus ensuring reproducible positioning of the patient even over several treatment cycles. The radio-oncology head positioning device can be detachably attached to the head support region via guide elements and guide pins to reduce backlash.

The head support region may comprise a locking device that allows the head support region to be adjustably supported at different angular positions relative to the torso support region.

The torso support area may comprise positioning elements to which a knee positioning device can be releasably attached. The torso support region may comprise positioning elements on which a pelvis positioning device can be releasably arranged. The positioning elements may be recesses, for example semicircular recesses at the edge of the torso support region, at which the knee positioning device and/or the pelvic positioning device may be releasably arranged.

In one embodiment, the torso support region may comprise a shoulder support region that comprises second positioning elements for a neck positioning device. The shoulder support region may alternatively or additionally comprise second positioning elements for a shoulder positioning device.

The second positioning devices may be cylindrical recesses for the inserts for shoulder and/or neck.

The first positioning elements may be positioning elements for positioning systems, knee braces, pelvic support devices, or the like.

The head positioning device and/or the patient positioning device may be at least partially made of carbon. First, this reduces weight such that the head positioning device as well as the patient positioning device are more easily handled by staff. Further, carbon materials affect radio-oncological treatment to a lesser extent than metal materials.

The inventor of the present invention refers to the patient positioning device according to the present invention as the Offenburg multi-position board made of carbon. This allows all radiation techniques to be performed on one patient positioning device. The board is completely radiolucent as it comprises no metal.

The base plate can extend under the torso support area and under the head support area at least partially. The base board may extend under the entire torso support area and head support area.

A radio-oncology head positioning device configured to support a patient's head during radio-oncology treatment comprises a base plate, at least one support member, a first U-shaped frame, a second U-shaped frame, and two first L-shaped attachment members. The base plate may comprise coupling elements for coupling the radio-oncology head positioning device to a radio-oncology patient positioning device. The at least one support member extends from the base plate. The back of the patient's head is directed toward the base plate during treatment. The at least one support element extends substantially adjacent the patient's head away from the base plate. For example, four columnar support elements may be used. In another embodiment, two cuboid support elements or three cuboid support elements may be used.

The first U-shaped frame is disposed on the at least one support element. The first U-shaped frame may be rigidly arranged on the at least one support element. The second U-shaped frame is detachably arranged on the first U-shaped frame. The two first L-shaped fastening members are arranged on the second U-shaped frame.

A occipital mask can be arranged between the first U-shaped frame and the second U-shaped frame. A face mask can be arranged on the two L-shaped fastening elements. The radio-oncological head positioning device according to the present invention allows that the face mask and the back of the occipital mask are stably supported, and thus the patient's head is reproducibly supported at the two first L-shaped fastening elements even over several treatments. A neck cushion may be arranged on the base plate to increase the comfort of the patient.

In one embodiment, two second L-shaped fastening elements are detachably arranged. One second L-shaped fastening element is arranged on each first L-shaped fastening element. In a preferred embodiment, the longer leg of the second L-shaped fastening element is arranged above the longer leg of the first L-shaped fastening element. In this embodiment, the shorter leg of the second L-shaped fastening element is arranged above the shorter leg of the first L-shaped fastening element.

The first and second L-shaped fastening elements are arranged on the side of the second U-shaped frame opposite to the base plate. Also, the second U-shaped frame is arranged on the side of the first U-shaped frame opposite to the base plate. The legs of the first and second L-shaped fastening members are arranged over the legs of the second U-shaped frame. The shorter legs of the two first L-shaped fastening members may be arranged over the middle leg of the second U-shaped frame. The longer legs of the two first L-shaped fastening members may be disposed on the legs of the second U-shaped frame extending from the middle leg (or the other two legs connecting legs) of the second U-shaped frame. The two second L-shaped attachment members allow the face mask to be securely attached to the first L-shaped attachment members.

In one embodiment, the radio-oncological head positioning device may comprise a slidable clamping member slidable in a longitudinal direction of the first U-shaped frame and in a longitudinal direction of the second U-shaped frame. The longitudinal direction is defined as the direction in which the first U-shaped frame and the second U-shaped frame are open. In its closed position, the clamping element presses the two first L-shaped fastening elements against the second U-shaped frame. In this position, a face mask is held between the two L-shaped fastening elements and the second U-shaped frame. In its open position, the clamping element is positioned behind the two L-shaped fastening elements as viewed longitudinally from the open end of the first U-shaped frame and the second U-shaped frame. The clamping element allows for easy and quick fixation of the first L-shaped fastening elements and the face mask. It is understood that the face mask can be fixed by means of screws or bolts inserted into openings extending through the second L-shaped fixing elements and first L-shaped fixing elements.

The invention also relates to a radio-oncology head positioning device adapted to hold a patient's head during radio-oncology treatment, comprising a base plate, two first L-shaped fastening elements and two second L-shaped fastening elements. The base plate is configured to couple to a radio-oncology patient positioning device, for example, the base plate may comprise coupling elements. The two first L-shaped fastening elements are arranged on the base plate. The first L-shaped fastening elements may be releasable or fixed.

The second L-shaped fastening elements are detachably arranged on the first L-shaped fastening elements. A face mask can be arranged between the first L-shaped fastening elements and the second L-shaped fastening elements.

The base plate may comprise receiving elements, for example, openings, recesses, or the like, configured to position a neck pillow.

The radio-oncological head positioning device may further comprise a clamping element that is slidable in a longitudinal direction of the radio-oncological head positioning device. In its closed position, the slidable clamping element presses the two first L-shaped fastening elements against the base plate. In its open position, the displaceable clamping element is located behind the two first L-shaped fastening elements as viewed in the longitudinal direction from the open end of the two first L-shaped fastening elements.

In both embodiments of the head positioning device, the two first L-shaped fastening elements and the second second L-shaped fastening elements are arranged such that they form a substantially U-shaped configuration when viewed from above. In other words, the long legs of the first L-shaped fastening elements are arranged in a substantially parallel arrangement and the short legs of the L-shaped fastening elements are arranged in a substantially collinear arrangement. Similarly, the long legs of the second L-shaped fastening members are arranged in parallel and the short legs of the L-shaped fastening members are arranged in substantially collinear arrangement.

The invention also relates to a radio-oncology patient positioning device made of carbon. The inventor of the present invention refers to the patient positioning device according to the present invention as an Offenburg multi-position board made of carbon. This allows all radiation techniques to be performed on one patient positioning device. The board is completely radiolucent since it comprises no metal.

The applicant reserves the right to claim protection separately on the head positioning device.

BRIEF DESCRIPTION OF THE FIGURES

The invention is now described with reference to the accompanying figures, which show exemplary and non-limiting embodiments of the invention, wherein.

DETAILED DESCRIPTION OF THE FIGURES

Exemplary embodiments of the invention are described below to facilitate understanding of the invention. It is understood that the figures are not to scale. It is also understood that spatial indications are for descriptive purposes and are not necessarily limiting.

Figure 1:
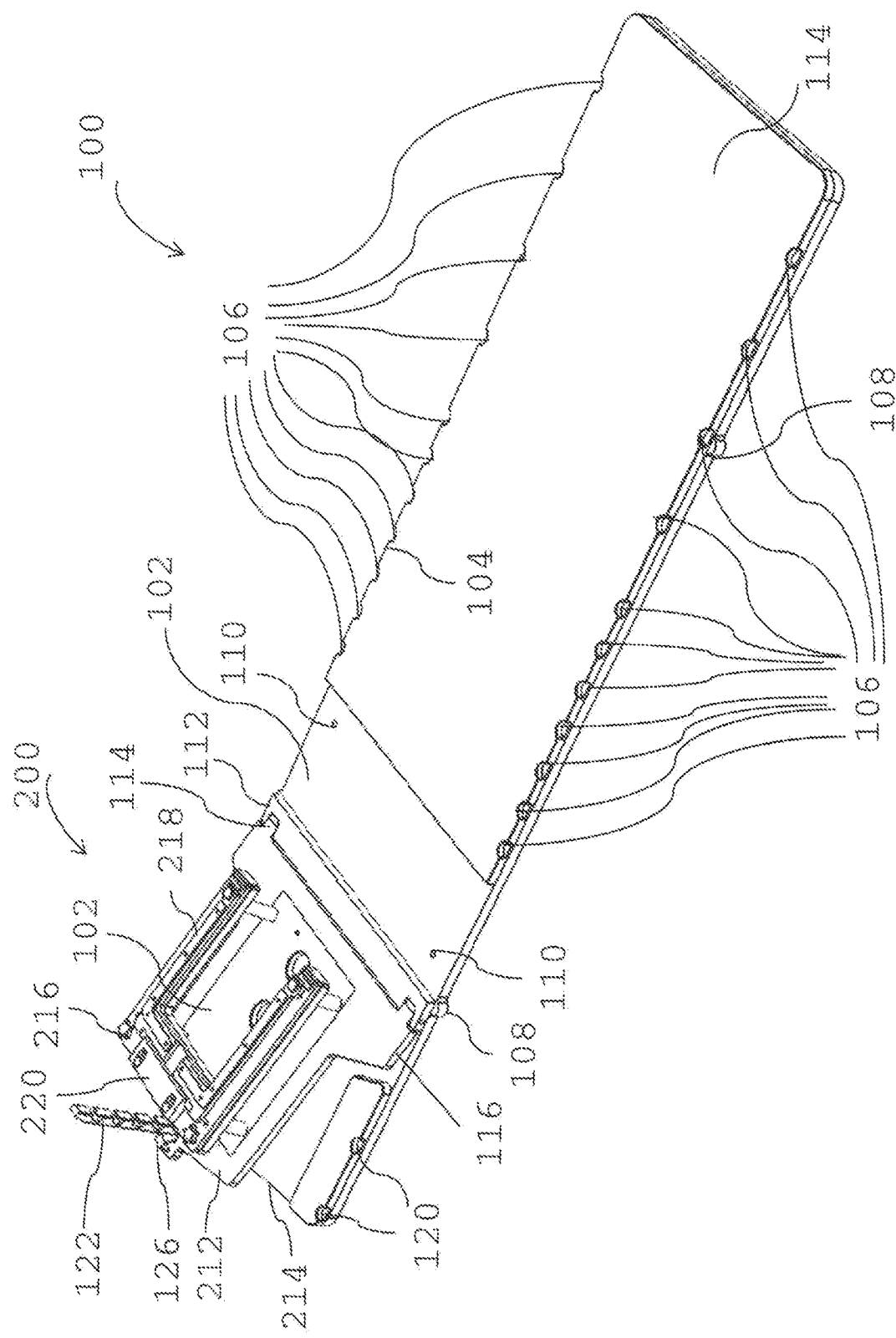
FIG. 1 shows a perspective top view of a radio-oncology patient positioning device.
Figure 2:
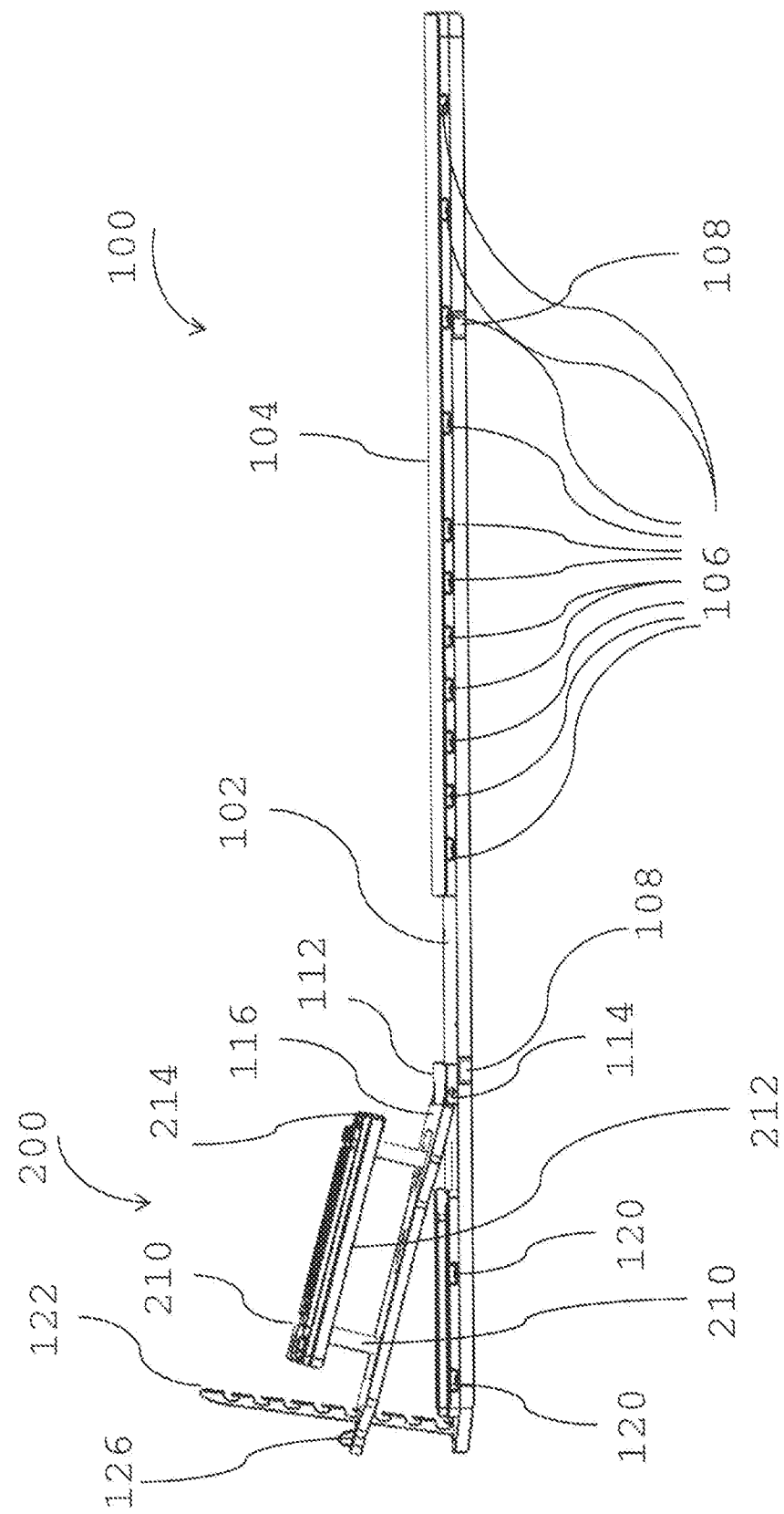
FIG. 2 shows a perspective side view of the radio-oncology patient positioning device.
Figure 3:
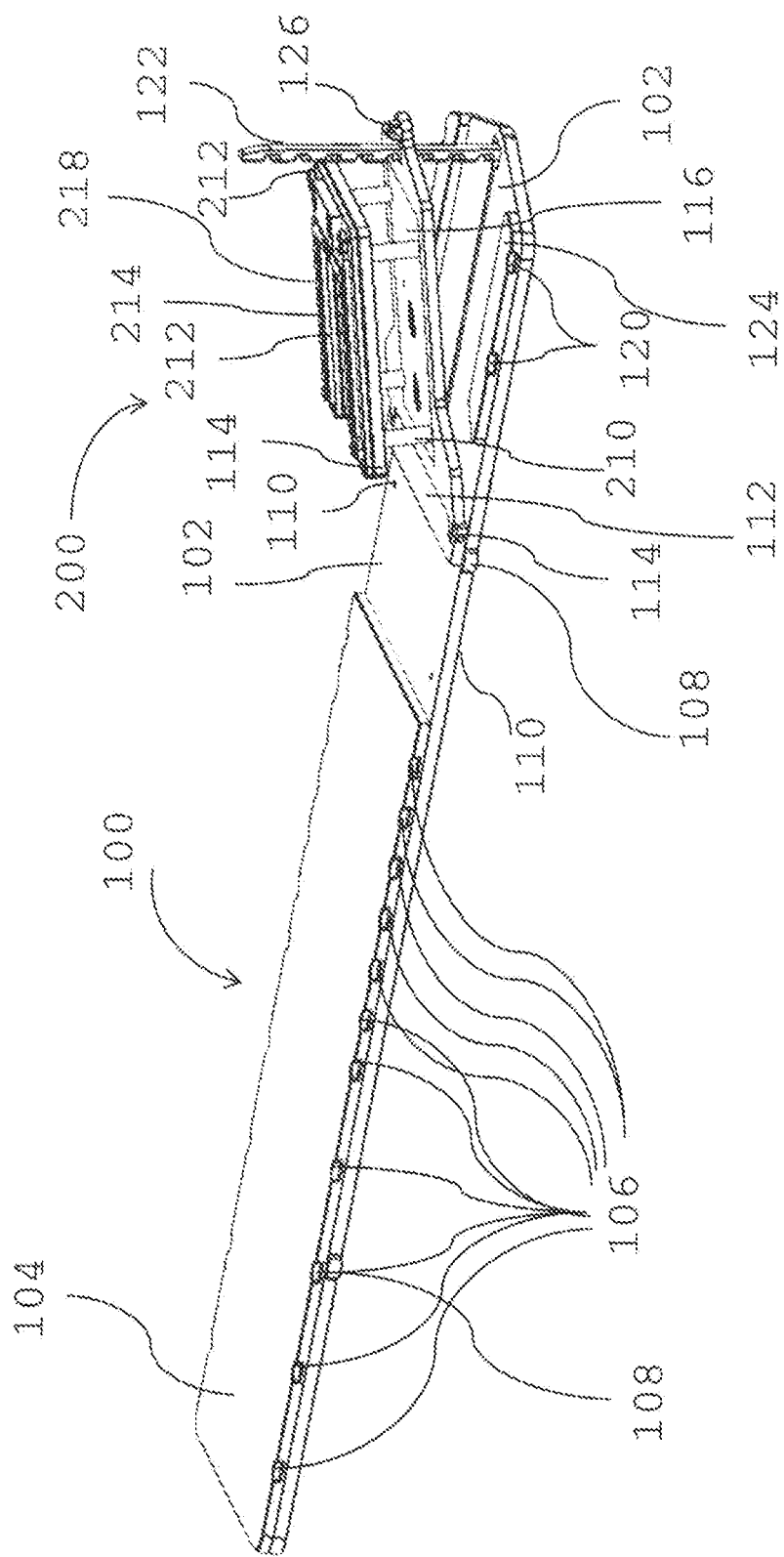
FIG. 3 shows another perspective view of the radio-oncology patient positioning device, in which a head positioning device is shown in more detail.

FIGS. 1, 2 and 3 illustrate a radio-oncology patient positioning device (hereinafter patient positioning device) 100 according to the present invention with a radio-oncology head positioning device (hereinafter head positioning device) 200 according to the present invention. The radio-oncological patient positioning device 100 and the radio-oncological head positioning device 200 are adapted to reproducibly position a patient and the patient's head during a radio-oncological treatment, in particular during a treatment cycle comprising several treatments in a predetermined period of time, for example several days, several weeks. In other words, the patient is positioned on the patient positioning device 100 prior to treatment and is released from the patient positioning device 100 after treatment. For the next treatment, the patient must again be reproducibly positioned on the patient positioning device 100 in the same position.

The patient positioning device 100 comprises a base plate 102 on which a front mounting plate 104 is disposed. The base plate 102 and the front mounting plate are substantially rectangular in shape, and the mounting plate 104 is disposed on the base plate 102, which comprises a larger surface area than the mounting plate 104. Device positioning elements 108 are formed on the base plate 102 and are provided for reproducibly and accurately positioning the base plate in a radio-oncology treatment device. The device positioning elements 108 extend in a semi-circular manner from the base plate 102.

A plurality of semi-circular recesses 106 are disposed on the front mounting plate 104, wherein, in use, positioning systems for positioning the knees, feet, pelvis, or the like may be disposed on the semi-circular in recesses 106.

The front mounting plate 104 is disposed at the region of the base plate 102 from which a patient's chest, pelvis, legs, and feet are supported. In the embodiment shown in FIGS. 1 to 3, the front mounting plate or torso support region 104 does not extend to the region, where the patient's shoulder and neck are in use. Cylindrical depressions 110 are formed at the region where the patient's neck and shoulder are located, which are provided to hold support devices for the patient's shoulder and support means for the patient's neck.

The base plate 102 extends below the head positioning device 200, wherein two of the mounting plates 124 having semi-circular and recesses 120 are disposed laterally of the head positioning device 200.

On the base plate 102 a joint receiving block 112 is disposed, which is supported by two joints 114. By means of the joints, a head plate 116 is pivotally supported on the bearing receiving block 112. The inclination of the head plate 116 can be reproducibly set at a predetermined angle by means of a detent bar 122, which is pivotally arranged on the base plate 102. A resilient locking means 126 prevents the detent bar 122 and the head plate 116 from moving.

In that the head plate is non-releasably (fixedly) pivotally connected to the base plate 102 by means of joints 114, the position of the head plate 116 is fixed without backlash and reproducibly with respect to the base plate 102 and the device mounting elements 108 and mounting elements 106, 120.

The base plate 102, the front mounting plate 104, the rear mounting plates 124 and/or the head plate 116 may be made of carbon. Thus, in one aspect, the patient positioning device 100 according to the present invention is particularly lightweight and can be handled with little effort by medical staff. The recesses 106, 120 have the advantage that further positioning devices can be positioned precisely and reproducibly.

Figure 4:
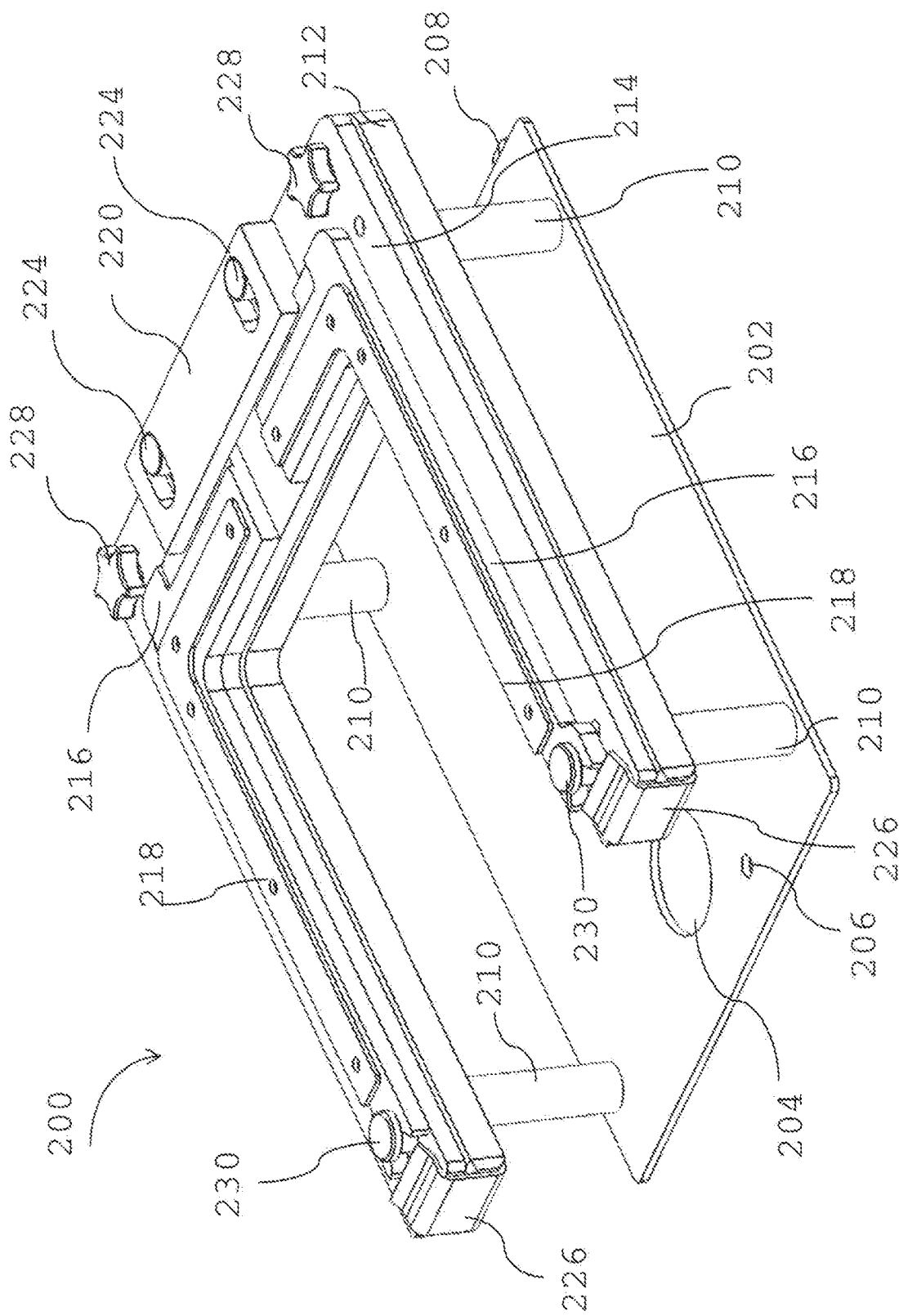
FIG. 4 shows a perspective view of a head positioning device.
Figure 5:
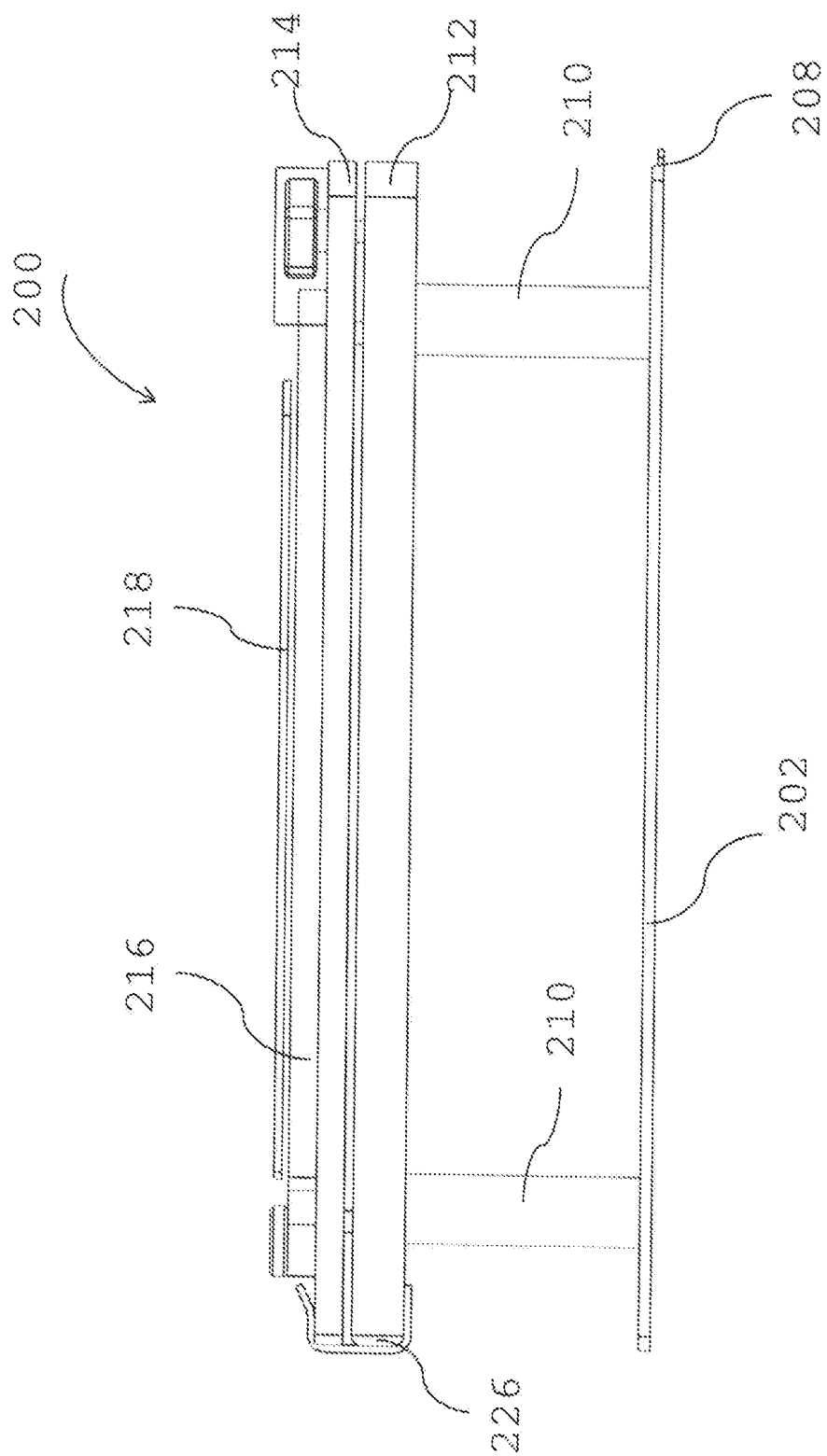
FIG. 5 shows a side view of the head positioning device.
Figure 6:
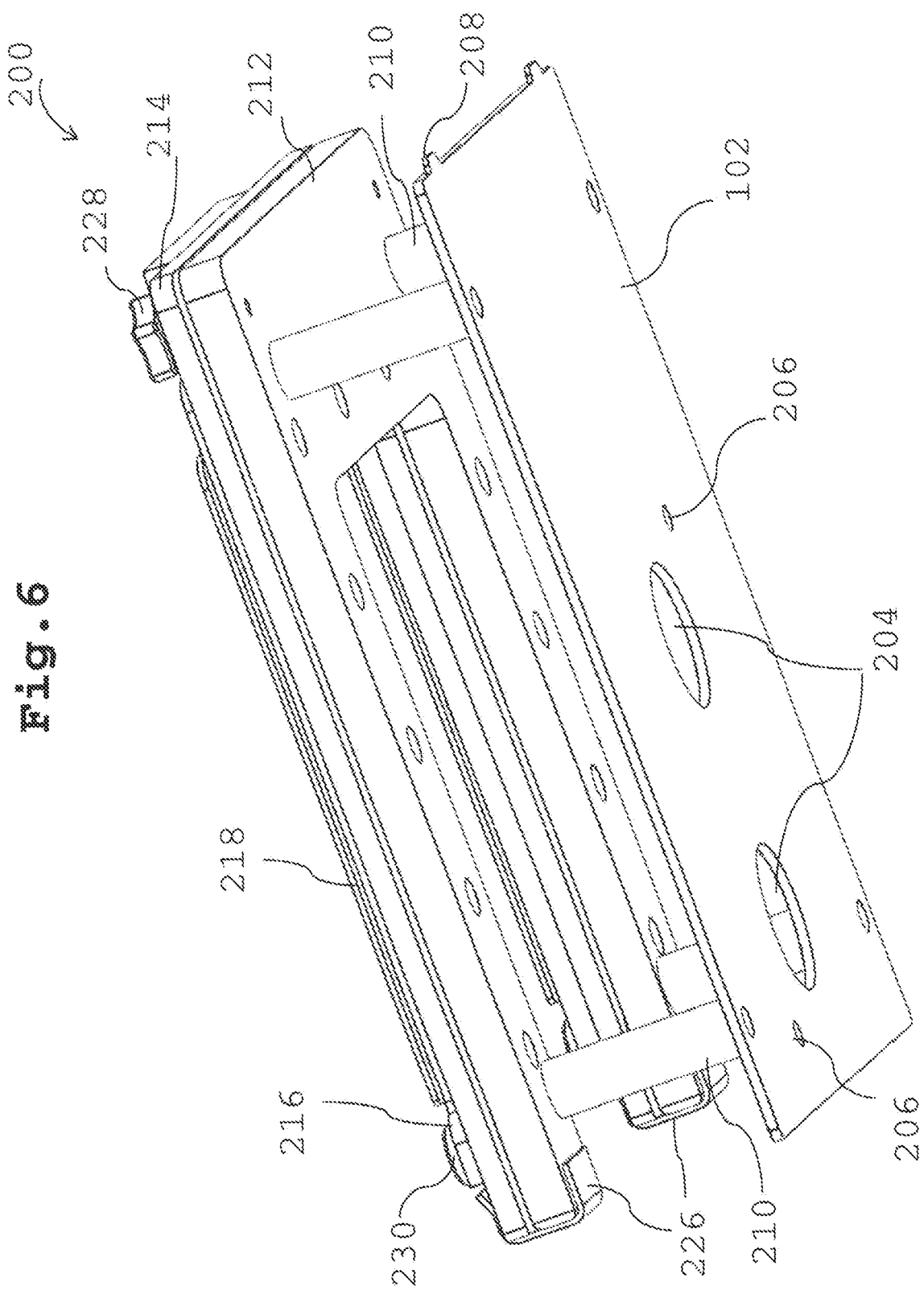
FIG. 6 shows a perspective view of the head positioning device from below.

With reference to FIGS. 4 to 6, a first embodiment of a radio-oncology head positioning device 200 (hereinafter head positioning device) is described. The head positioning device 102 comprises a base plate 202 having lugs 208 disposed at the front end of the base plate. The base plate comprises mounting apertures 206. The lug 208 can be inserted into a complementary opening in the head plate 106 of the patient positioning device 100. Next, the base plate 202 is pivoted into the receiving opening for the base plate 202. Next, the base plate 202 is secured to the head plate 116 by screws extending through the mounting apertures 206 of the base plate 202.

The base plate 202 further comprises positioning openings 204, at which, for example, a neck cushion can be arranged.

In the first embodiment of the head positioning device 200, support elements 210 extend from the base plate. In use, the support elements 210 extend adjacent a patient's head (not shown). A first U-shaped frame 212 is attached to the support elements 210. The first U-shaped frame is open toward the base plate of the patient positioning device 100. A second U-shaped frame 214 is arranged above the first U-shaped frame 212, which is pressed against the first U-shaped frame 212 by means of at least one rotary knob 218. In use, an occipital mask may be disposed between the first U-shaped frame 212 and the second U-shaped frame 214 to support the back of a patient's head in use. The first U-shaped frame 212 and the second U-shaped frame 214 are held together by clips 226.

Two first L-shaped fastening members 216 may be disposed on the second U-shaped frame 214. The two first L-shaped fastening elements 216 each comprise a recess 222 into which a clamping element 220 can be slid in the longitudinal direction of the head positioning device 200 and the patient positioning device 100, respectively. The clamping element 220 can engage the recesses 222 of the first L-shaped mounting elements such that the first L-shaped mounting elements 222 are urged toward the second U-shaped frame 214. The clamping element 220 is supported by pins 224 in the second U-shaped frame 214.

Second L-shaped fastening elements 218 are attached to the first L-shaped fastening elements 216. The second L-shaped fastening members 218 may be secured to the first L-shaped fastening members 216 by screws extending through the openings 232 in the second L-shaped fastening members. A face mask may be clamped between the first L-shaped mounting members 216 and the second L-shaped mounting members 218. Prior to arranging the face mask, the mask is heated using a water bath having a temperature of about 65° C.

In the embodiment shown in FIGS. 4 to 6, the first U-shaped frame 212 and the second U-shaped frame 214 are open in the longitudinal direction of the head positioning device 200 and the patient positioning device 100, respectively. The long legs of the two first L-shaped attachment members 216 and the long legs of the two second L-shaped attachment members 218 are also directed in the longitudinal direction of the head positioning device 200 and the patient positioning device 100, respectively.

The head positioning device 200 may be made of carbon.

Figure 7:
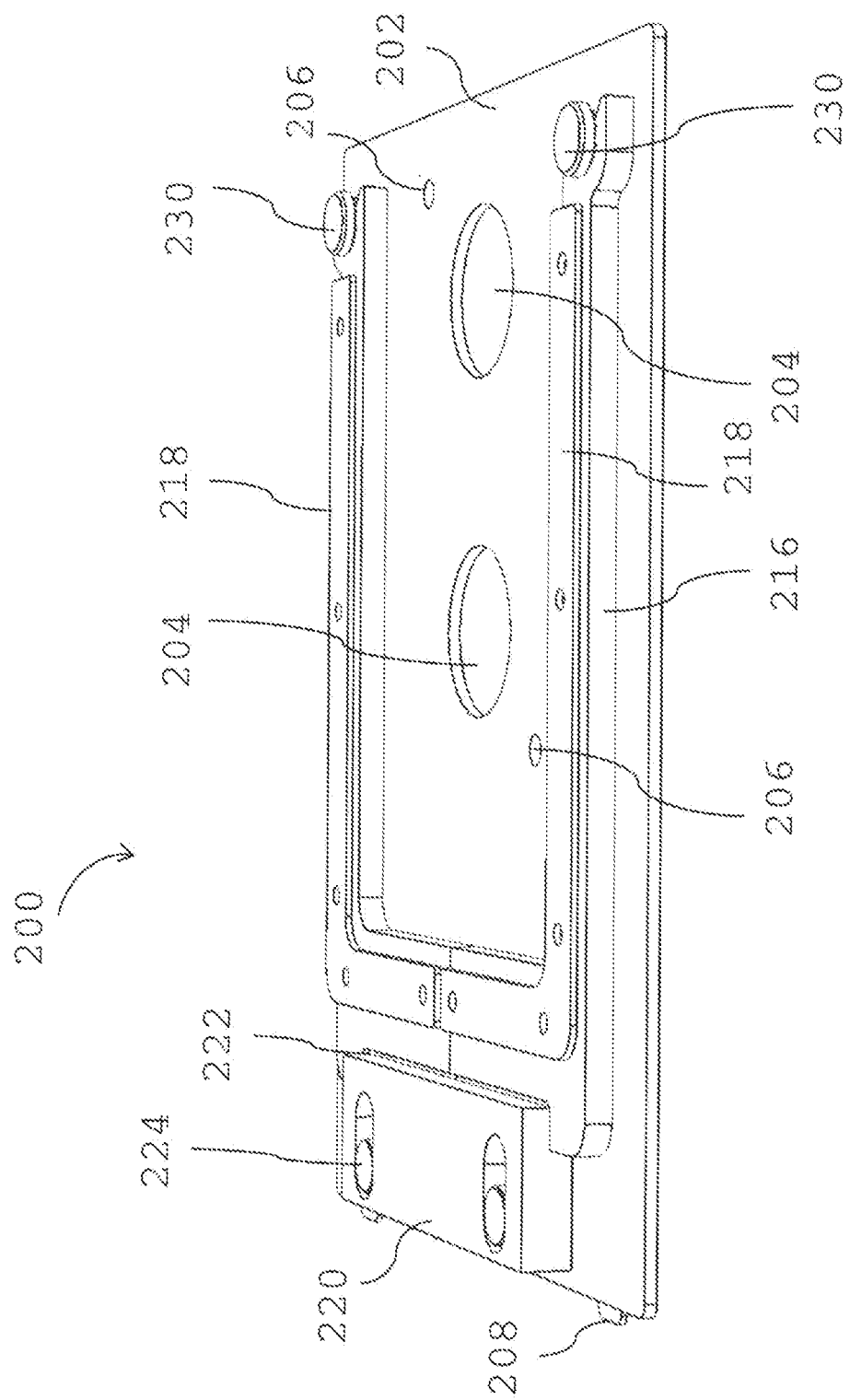
FIG. 7 shows another embodiment of the head positioning device.

FIG. 7 shows a second embodiment of the positioning device 200' according to the present invention, which essentially corresponds to the first embodiment 200 described above with reference to FIGS. 4 to 6. Consequently, for the sake of conciseness, only the differences between the second embodiment 200' and the first embodiment 200 of the head positioning device according to the present invention will be described.

The first L-shaped fastening elements 218 are fastened to the base plate 202 by means of a stop 230 and a clamping element 222, the function of which corresponds to that described with reference to FIGS. 4 to 6 with respect to the first embodiment 200. A face mask, also referred to as a front head mask, may be disposed between the first L-shaped attachment members 216 and the second L-shaped attachment members 218. The patient's head may rest on a pillow attached to the attachment apertures 204.

The base plate 202 is disposed in a clearance-free manner by means of lugs 208 in an opening in the head plate 116 of the patient positioning device 100, and is disposed in a clearance-free manner on the head plate 116 by means of screws extending through the attachment openings 206 of the base plate 202.

Also in this embodiment, the long legs of the first two L-shaped fastening devices 216 and the second L-shaped fastening devices 218 extend in the longitudinal direction of the head positioning device 200' and patient positioning device 200', respectively.

The second embodiment of the head positioning device 200' may be made of carbon.

The present invention has the advantage that the head positioning device 200, 200' can be used to position a patient's head in a reproducible manner. The head positioning device 200, 200' can be flexibly adapted to the needs of a patient by a medical personnel. Furthermore, the head positioning device 200, 200' according to the present invention can be made ready for use in a short time, which is particularly relevant for multiple treatments.

The head positioning device 200, 200' and the patient positioning device 100 as well as the support devices attached thereto (not shown) are adapted to the patient at the beginning of a treatment period and are not changed during the treatment period. Thus, on the one hand, the accuracy of the treatment can be increased over the entire treatment period and, on the other hand, the set-up time for each irradiation within the treatment period can be reduced, as well as the staff can be relieved.

Furthermore, the patient positioning device according to the present invention comprises the advantage that the head positioning device can be arranged without backlash and reproducibly with respect to the base plate 102 of the patient positioning device 100 by means of the joints 114 of the head plate 216, thereby increasing the quality of the medical treatment.

In the cranial region, both anterior head masks can be made in the embodiment of the head positioning device 200' according to FIG. 7 and full cranial masks can be made in the embodiment of the head positioning device 200 according to FIG. 4.

For attaching the front head mask in the head positioning device 200' according to FIG. 7, a mask material is screwed onto the first L-shaped fastening elements 216 through the second L-shaped fastening elements 218 by means of plastic screws. The mask material is heated by means of an approximately 65° C. water bath and placed over the front of the patient's skull and molded on. After approx. 1 minute, the mask material is cured. The first L-shaped fastening element 216 is precisely positioned on the base plate 202 using two mushroom heads (stops) 230 and a clamping block (clamping element) 220. The back of the head rests on a neck cushion, which is fixed in place by means of the fastening opening 204.

In the case of full-head masks, the back of the head is positioned unsupported by means of the head positioning device 200 as shown in FIG. 4. The base plate 202, the support elements 210 and the first U-shaped frame 212 form a fixed unit that always remains in this state. The first U-shaped frame 212 and the second U-shaped frame 214 form a sandwich mount into which the preheated mask material is clamped and individually adapted to the occiput of a patient. The second U-shaped frame 216 is attached to the first U-shaped frame using the twist knob 228 and clips 226. Positioning pins on the first U-shaped frame 212 and complementary openings 227 on the second U-shaped frame 214 allow for reproducible positioning of the two U-shaped frames relative to each other.

The front head mask is then fabricated. This is done immediately following the fabrication of the occipital mask, while the patient is then lying in the occipital mask. For the front head mask, a mask material is arranged on the first L-shaped fastening elements 216 and fastened by the second L-shaped fastening elements 218 using plastic screws. The mask material is heated by means of an approximately 65° C. water bath and is placed over the front of the patient's skull and molded in place. After about 1 minute, the mask material is cured. The first L-shaped attachment elements 216 are then attached to the second U-shaped frame 214. Thereby, the first L-shaped fastening elements 216 are precisely positioned on the head positioning device 200 and the second U-shaped frame 214, respectively, by two mushroom heads (stops) 230 and a clamping block (clamping element) 220.

Both skull masks can be used together or individually.

Additionally, shoulder mask device can be applied to precisely fix the skull, neck and shoulder. The shoulder mask device is inserted into the base plate 102 (recess 102) and fixed in place by pins in the recesses 110.

Then, using the same principle as the skull masks, the mask is also additionally positioned over the shoulders.

The base plate 102 can be positioned precisely and reproducibly on the table top of the irradiation unit. A detent bar 122 can be used to adjust different angles for skull tilt by holding the tilt member 116 in the recesses of the detent bar 122 via hinges 114.

Via the positioning elements 106 on the mounting plate 104, further holders can also be arranged on the patient positioning device 100 by other companies. By means of these holders, among other things, the legs are positioned in the respective patient positioning device via a commercially available leg holder.

The present invention relates to a radio-oncological patient positioning device made of carbon, which for the first time combines a head positioning device, which allows the use of a high-precision double mask (occiput and face) suitable for stereotactic radiotherapy, with a tiltable plate fixed to the positioning device.

This results in significant advantages for the daily practice of radiotherapy. Certain positioning positions of the patient, which are advantageous for the protection of sensitive tissue with simultaneous application of a high radiation dose in the tumor, can be achieved at all with the necessary precision by the present invention. The use of carbon allows all parts of the device to be radiated through without significant weakening of the dose while maintaining the highest precision of the bearing. The concept of integrating multiple support structures, which is the basis of the invention, eliminates the need to rebuild the radiation table for each patient. This increases precision, as each time a new positioning device is set up, errors are introduced that are incompatible with the requirements of high-precision irradiations. Furthermore, the invention facilitates the daily work of radiation therapy staff. The exact reproducibility of the patient position is improved by the present invention (for the first time combination of a reproducible high-precision, two-part mask with a tiltable positioning board). The invention integrates very easy-to-use fixation devices (mechanisms for engaging masks and other positioning aids). These devices allow the mask to be made quickly, such that patients have substantially reduced lying times during this procedure, which is a great advantage for critically ill patients with brain tumors who are supported in such masks. The same devices for accurately engaging and securing the precision mask likewise allow for significant time savings in reproducing patient positioning on a daily basis. The invention allows the combination of different components for patient positioning, for example, board or plate for shoulder positioning and high-precision positioning mask. This is not possible in such a flexible way with previous positioning devices.

The invention claimed is:

1. A radio-oncological patient positioning device, comprising
    a torso support region adapted to support a torso of a patient, comprising
    first positioning members adapted to releasably arrange
    a knee positioning means and/or
    a pelvic positioning device;
    a shoulder support portion having second positioning members adapted to releasably arrange
    a neck positioning means; and/or
    a shoulder positioning device; and
    a head support portion; characterized in that: the head support portion is pivotally disposed, by means of at least one joint, on the shoulder support portion or on a base plate on which the torso support region is disposed; and
    wherein the head support portion is adapted such that a radio-oncological head positioning device is detachably attachable to the head support portion, wherein an occipital mask and/or a face mask is arrangeable on the head positioning device, the radio-oncological patient positioning device further characterized by two second L-shaped attachment members removably disposed on the two first L-shaped attachment members.

2. The radio-oncological patient positioning device according to claim 1, wherein the head support portion comprises a locking device, which enables the head support portion to be adjustably supported at different angular positions relative to the torso support region.

3. The radio-oncology patient positioning device according to claim 1, wherein the base plate extends at least partially below the torso support region and below the head support portion.

4. The radio-oncology patient positioning device according to claim 1, wherein the radio-oncology head positioning device is adapted to support a head of the patient during radio-oncology treatment; and further comprises:
    a base plate adapted to couple to the radio-oncology patient positioning device;
    at least one support member extending from the base plate; and
    a first U-shaped frame disposed on the at least one support member; and
    a second U-shaped frame releaseably disposed on the first U-shaped frame; and
    two first L-shaped attachment members disposed on the second U-shaped frame.

5. The radio-oncological patient positioning device according to claim 4, characterized in that between the first U-shaped frame and the second U-shaped frame the occipital mask is arrangeable.

6. The radio-oncology patient positioning device according to claim 1 characterized by a clamping member slidable in a longitudinal direction of the first U-shaped frame and the second U-shaped frame, which in a closed position presses the two first L-shaped fastening elements against the second U-shaped frame and in an open position is arranged behind the two first L-shaped fastening elements as viewed in the longitudinal direction from the open end of the first U-shaped frame and the second U-shaped frame.

7. The radio-oncological patient positioning device according to claim 6, characterized in that between the first L-shaped mounting elements and the second L-shaped mounting elements the face mask is arrangeable.

8. The radio-oncological patient positioning device according to claim 1, wherein the radio-oncological head positioning device adapted to hold a head of the patient during a radio-oncological treatment; and further comprises:
    a base plate adapted to be coupled to a radio-oncology patient positioning device; and
    two first L-shaped fastening members disposed on the base plate; and
    two second L-shaped fastening members releasably disposed on the first L-shaped fastening members;
    wherein the facemask is disposable between the first L-shaped mounting members and the second L-shaped mounting members.

9. The radio-oncological patient positioning device according to claim 8, characterized by a clamping element displaceable in a longitudinal direction of the radio-oncological head positioning device, which in a closed position presses the two first L-shaped fastening elements against the base plate and in an open position is arranged behind the two first L-shaped fastening elements as viewed in the longitudinal direction from the open end of the two first L-shaped fastening elements.

10. A radio-oncological patient positioning device, comprising
    a torso support region adapted to support the torso of a patient, comprising
    first positioning members adapted to releasably arrange
    a knee positioning means and/or
    a pelvic positioning device;
    a shoulder support portion having second positioning members adapted to releasably arrange
    a neck positioning means; and/or
    a shoulder positioning device; and
    a head support portion; characterized in that: the head support portion is pivotally disposed, by means of at least one joint, on the shoulder support portion or on a base plate on which the torso support region is disposed; and wherein the head support portion is adapted such that a radio-oncological head positioning device is detachably attachable to the head support portion, wherein an occipital mask and/or a face mask is arrangeable on the head positioning device, wherein the radio-oncological head positioning device adapted to hold a head of the patient during a radio-oncological treatment; and further comprises:

a base plate adapted to be coupled to a radio-oncology patient positioning device; and two first L-shaped fastening members disposed on the base plate; and two second L-shaped fastening members releasably disposed on the first L-shaped fastening members;

wherein the facemask is disposable between the first L-shaped mounting members and the second L-shaped mounting members.

11. The radio-oncological patient positioning device according to claim 10, wherein the head support portion comprises a locking device, which enables the head support portion to be adjustably supported at different angular positions relative to the torso support region.

12. The radio-oncology patient positioning device according to claim 10, wherein the base plate extends at least partially below the torso support region and below the head support portion.

13. The radio-oncology patient positioning device according to claim 10, wherein the radio-oncology head positioning device is adapted to support a head of the patient during radio-oncology treatment; and further comprises:

a base plate adapted to couple to a radio-oncology patient positioning device;

at least one support member extending from the base plate; and a first U-shaped frame disposed on the at least one support member; and a second U-shaped frame releaseably disposed on the first U-shaped frame; and two first L-shaped attachment members disposed on the second U-shaped frame.

14. The radio-oncology patient positioning device according to claim 13, characterized by two second L-shaped attachment members removably disposed on the two first L-shaped attachment members.

15. The radio-oncology patient positioning device according to claim 14, characterized by a clamping member slidable in a longitudinal direction of the first U-shaped frame and the second U-shaped frame, which in a closed position presses the two first L-shaped fastening elements against the second U-shaped frame and in an open position is arranged behind the two first L-shaped fastening elements as viewed in the longitudinal direction from the open end of the first U-shaped frame and the second U-shaped frame.

16. The radio-oncological patient positioning device according to claim 13, characterized in that between the first U-shaped frame and the second U-shaped frame the occipital mask is arrangeable.

17. The radio-oncological patient positioning device according to claim 15, characterized in that between the first L-shaped mounting elements and the second L-shaped mounting elements the face mask is arrangeable.

18. The radio-oncological patient positioning device according to claim 17, characterized by a clamping element displaceable in a longitudinal direction of the radio-oncological head positioning device, which in closed position presses the two first L-shaped fastening elements against the base plate and in an open position is arranged behind the two first L-shaped fastening elements as viewed in the longitudinal direction from the open end of the two first L-shaped fastening elements.

* * * * *